US011116593B2

(12) United States Patent
Hashimoto et al.

(10) Patent No.: US 11,116,593 B2
(45) Date of Patent: Sep. 14, 2021

(54) ROBOT SYSTEM

(71) Applicant: KAWASAKI JUKOGYO KABUSHIKI KAISHA, Kobe (JP)

(72) Inventors: Yasuhiko Hashimoto, Kobe (JP); Masayuki Kamon, Akashi (JP); Shigetsugu Tanaka, Akashi (JP)

(73) Assignee: KAWASAKI JUKOGYO KABUSHIKI KAISHA, Kobe (JP)

(*) Notice: Subject to any disclaimer, the term of this patent is extended or adjusted under 35 U.S.C. 154(b) by 307 days.

(21) Appl. No.: 15/755,108

(22) PCT Filed: Jun. 24, 2016

(86) PCT No.: PCT/JP2016/003061
§ 371 (c)(1),
(2) Date: Feb. 26, 2018

(87) PCT Pub. No.: WO2017/033377
PCT Pub. Date: Mar. 2, 2017

(65) Prior Publication Data
US 2018/0243902 A1    Aug. 30, 2018

(30) Foreign Application Priority Data

Aug. 25, 2015 (JP) .............................. JP2015-165479

(51) Int. Cl.
*B25J 9/16* (2006.01)
*A61B 34/37* (2016.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC ......... A61B 34/32; A61B 34/37; A61B 34/35; A61B 34/70; B25J 9/0081; B25J 9/1602;
(Continued)

(56) References Cited

U.S. PATENT DOCUMENTS 4,888,708 A * 12/1989 Brantmark ........... G05B 19/427
700/264
6,212,443 B1 * 4/2001 Nagata ................. G05B 19/423
700/245
(Continued)

FOREIGN PATENT DOCUMENTS

CN   104589304 A   5/2015
JP   S59-135507 A   8/1984
(Continued)

OTHER PUBLICATIONS

Sep. 27, 2016 International Search Report issued in International Patent Application PCT/JP2016/003061.
(Continued)

*Primary Examiner* — Jason Holloway
(74) *Attorney, Agent, or Firm* — Oliff PLC (57) ABSTRACT

A robot system which is capable of reducing an operator's workload and easily correcting preset operation of a robot. The robot system includes a robot main body having a plurality of joints, a control device configured to control operation of the robot main body and an operating device including a teaching device configured to teach the control device one of positional information on the robot main body and angular information on the plurality of joints so as to execute an automatic operation of the robot main body and a manipulator configured to receive a manipulating instruction from an operator to manually operate the robot main body or correct the operation of the robot main body under the automatic operation.

5 Claims, 9 Drawing Sheets

(51) Int. Cl.

| | |
|---|---|
| *G05B 19/418* | (2006.01) |
| *B25J 9/00* | (2006.01) |
| *B23P 19/04* | (2006.01) |
| *B25J 13/00* | (2006.01) |
| *B25J 19/04* | (2006.01) |
| *B25J 13/08* | (2006.01) |
| *B25J 3/00* | (2006.01) |
| *B25J 13/06* | (2006.01) |
| *B25J 18/00* | (2006.01) |
| *B25J 19/02* | (2006.01) |
| *B25J 3/04* | (2006.01) |
| *B23Q 15/12* | (2006.01) |
| *B25J 13/02* | (2006.01) |
| *B25J 11/00* | (2006.01) |
| *G06F 3/01* | (2006.01) |
| *H04N 5/232* | (2006.01) |
| *H04N 7/18* | (2006.01) |
| *A61B 34/32* | (2016.01) |
| *G06T 7/62* | (2017.01) |
| *G06T 7/70* | (2017.01) |
| *B23P 21/00* | (2006.01) |

(52) U.S. Cl.
CPC ................ *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1638* (2013.01); *B25J 9/1641* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC ........ B25J 13/088; B25J 18/00; B25J 9/1664; B25J 9/1689; B25J 13/06; B25J 9/1674; B25J 9/1641; B25J 9/1638; B25J 9/0087; B25J 9/1646; B25J 9/1653; B25J 9/1612; B25J 19/028; B25J 13/085; B25J 13/087; B25J 9/0084; B25J 9/1697; B25J 13/006; B25J 13/08; B25J 3/00; B25J 9/1669; B25J 9/1682; B25J 19/023; B25J 3/04; B25J 9/1633; B25J 9/1628; B25J 13/02; B25J 9/163; B25J 11/008; B25J 13/003; B25J 13/065; B25J 13/025; B25J 13/084; B25J 13/00; B25J 19/04; B25J 9/1692; B23Q 15/12; G05B 2219/39004; G05B 2219/39439; G05B 2219/33007; G05B 2219/40195; G05B 19/425; G05B 2219/40385; G05B 19/409; G05B 2219/36162; G05B 19/4182; G05B 2219/37297; G05B 2219/39102; G05B 2219/40143; G05B 2219/40182; G05B 2219/40145; G05B 2219/40387; G05B 2219/40139; G05B 2219/40161; G05B 2219/40146; G05B 2219/40627; G05B 2219/40022; G05B 2219/39531; G05B 2219/40163; G05B 2219/39533; G05B 2219/35464; G05B 2219/40142; G05B 2219/40169; G05B 2219/40183; G05B 2219/40134; G05B 2219/40162; G05B 2219/40136; Y10S 901/03; Y10S 901/04; Y10S 901/09; Y10S 901/47; Y10S 901/08; Y10S 901/27; Y10S 901/41; Y10S 901/10; Y10S 901/46; Y10S 901/02; G06T 7/62; G06T 7/70; G06F 3/017; H04N 5/23219; H04N 7/181; B23P 19/04; B23P 21/002; B23P 21/00; Y02P 90/02

See application file for complete search history.

(56) References Cited

U.S. PATENT DOCUMENTS

| | | | |
|---|---|---|---|
| 2004/0148058 A1* | 7/2004 | Johannessen | B25J 13/06 700/245 |
| 2004/0260426 A1* | 12/2004 | Johannessen | B25J 9/1674 700/245 |
| 2008/0125908 A1* | 5/2008 | Sjoberg | B25J 9/1674 700/247 |
| 2011/0054685 A1* | 3/2011 | Wada | B25J 9/1664 700/252 |
| 2012/0239194 A1* | 9/2012 | Kagawa | B25J 9/1692 700/254 |
| 2015/0239120 A1* | 8/2015 | Yamamoto | B25J 9/1602 700/247 |

(56) References Cited

U.S. PATENT DOCUMENTS

2016/0031077 A1* 2/2016 Inaba ................ B25J 9/1674
700/264
2017/0028557 A1* 2/2017 Battisti .............. B25J 9/0081

FOREIGN PATENT DOCUMENTS

| JP | S62-49403 A | 3/1987 |
| JP | H4-310396 A | 11/1992 |
| JP | H08-267381 A | 10/1996 |
| JP | 2003-311661 A | 11/2003 |
| JP | 2006-346827 A | 12/2006 |
| JP | 2011-224696 A | 11/2011 |
| JP | 2016-083713 A | 5/2016 |
| TW | 201446391 A | 12/2014 |

OTHER PUBLICATIONS

Sep. 27, 2016 Written Opinion issued in International Patent Application PCT/JP2016/003061.

Mar. 28, 2018 Office Action issued in Taiwanese Patent Application No. 105124427.

* cited by examiner

ROBOT SYSTEM

TECHNICAL FIELD

The present disclosure relates to a robot system.

BACKGROUND ART

Conventionally, an iterative work, such as welding, painting, assembling of components, and application of seal adhesive, is automatically performed in a manufacture site by an industrial robot. In order to make the robot to perform the work, the robot is necessary to be taught with information required for the work and store the information therein.

A method of teaching the robot includes, for example, teaching by a remote control using a teaching pendant (e.g., Patent Document 1).

REFERENCE DOCUMENT OF CONVENTIONAL ART

Patent Document

[Patent Document 1] JP2016-083713A

DESCRIPTION OF THE DISCLOSURE

Problems to be Solved by the Disclosure

Meanwhile, part of the operation taught to the robot may be necessary to be changed for various reasons. For example, when a work target, a work environment, etc. of the robot are partially changed from those when taught, problems, such as the robot becoming impossible to carry out the objective work, and the work accuracy being lowered, may arise.

Moreover, after finishing the teaching, a fault may be discovered in the initially-created teaching information for part of the work. In such a case, the teaching information to be used for an automatic operation of the robot is changed by again performing the teaching.

Additionally, in the teaching by the remote control using the teaching pendant, since position coordinates of the robot is inputted by the teaching pendant, many time and labors are required, and it is burdensome for the teacher. The same can be said for changing the part of robot operation (e.g., correcting the operation of the robot under the automatic operation).

Therefore, the purpose of the present disclosure is to provide a robot system, which is capable of reducing an operator's workload and easily correcting preset operation of a robot.

SUMMARY OF THE DISCLOSURE

In order to solve the above issue, a robot system according to the present disclosure includes a robot main body having a plurality of joints, a control device configured to control operation of the robot main body, and an operating device including a teaching device configured to teach the control device one of positional information on the robot main body and angular information on the plurality of joints so as to execute an automatic operation of the robot main body, and a manipulator configured to receive a manipulating instruction from an operator to manually operate the robot main body or correct the operation of the robot main body under the automatic operation.

Thus, an operator's workload is reduced and preset operation of the robot can easily be corrected.

Effect of the Disclosure

According to the robot system of the present disclosure, the operator's workload is reduced and the preset operation of the robot can easily be corrected.

MODES FOR CARRYING OUT THE DISCLOSURE

Hereinafter, embodiments of the present disclosure will be described with reference to the drawings. Note that, throughout the drawings, the same reference characters are assigned to the same or corresponding parts and redundant description is omitted. Further, throughout the drawings, components for describing the present disclosure are selectively illustrated and illustration of the other components may be omitted. Furthermore, the present disclosure is not limited to the following embodiments.

First Embodiment

A robot system according to a first embodiment includes a robot main body having a plurality of joints, a control device which controls operation of the robot main body, and an operating device having a teaching device which teaches the control device positional information on the robot main body or angular information on the plurality of joints so as to execute an automatic operation of the robot main body, and a manipulator which corrects the operation of the robot main body under the automatic operation.

Further in the robot system according to the first embodiment, the control device may include an adder which receives an operation instruction value for the robot main body in the automatic operation and a correction instruction value outputted from the manipulator, and adds the operation instruction value and the correction instruction value.

Moreover, in the robot system according to the first embodiment, the teaching device and the manipulator may be arranged in different casings, respectively.

Furthermore, in the robot system according to the first embodiment, the control device may include a switch device which switches an instruction value between an instruction value outputted from the adder and a teaching instruction value outputted from a teaching device therebetween, and outputs it to the robot main body.

Hereinafter, one example of the robot system according to the first embodiment will be described with reference to FIGS. 1 to 4.

[Configuration of Robot System]

Figure 1:
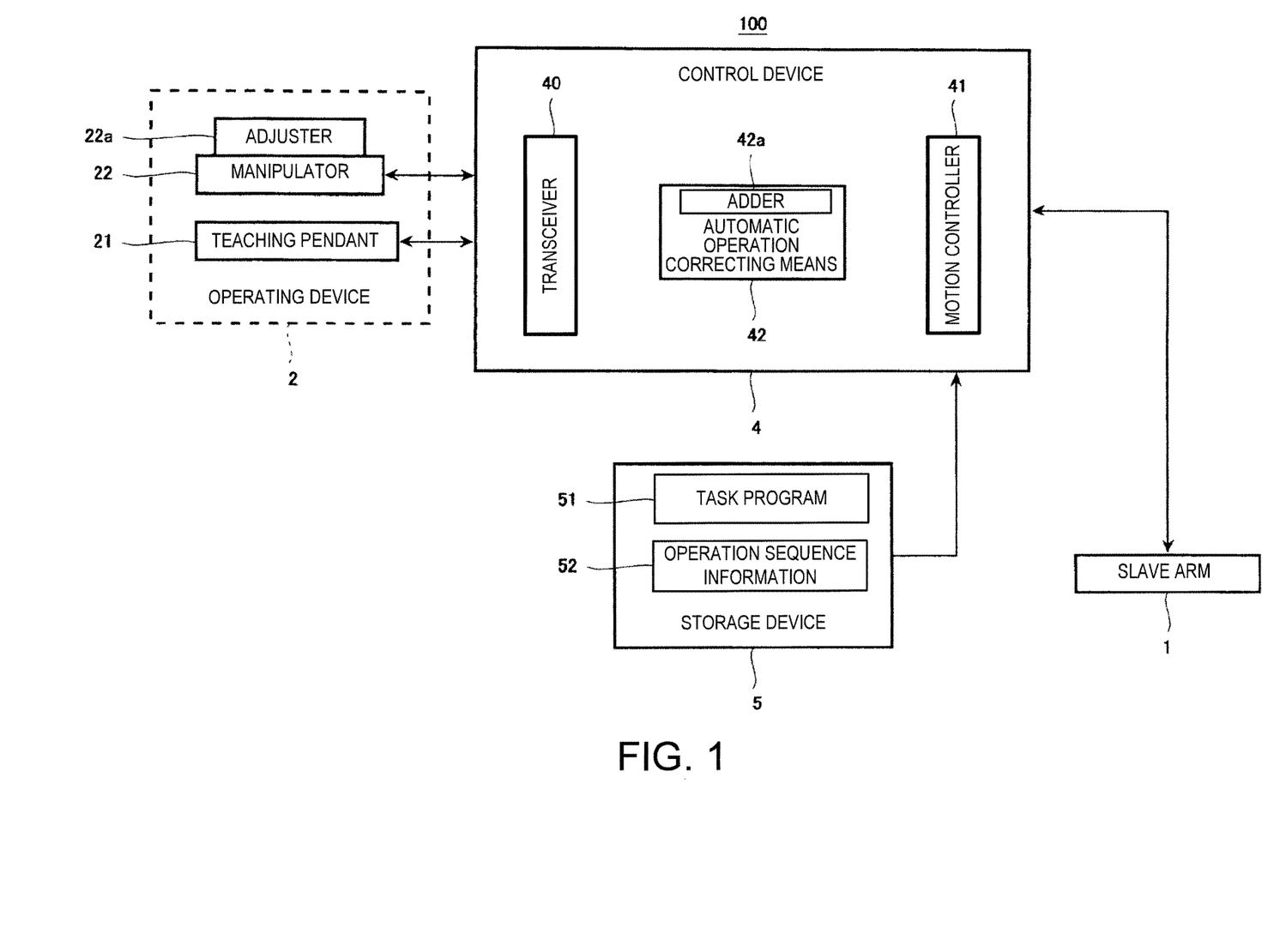
FIG. 1 is a block diagram illustrating a schematic configuration of a robot system according to a first embodiment.

FIG. 1 is a block diagram illustrating a schematic configuration of the robot system according to the first embodiment.

As illustrated in FIG. 1, a robot system 100 according to the first embodiment includes a slave arm (robot main body) 1, an operating device 2 having a teaching pendant (teaching device) 21 and a manipulator 22, a control device 4, and a storage device 5. It is possible to automatically operate the slave arm 1 by setting position coordinates of the slave arm 1 and/or an angle of each joint, etc. with the teaching pendant 21. Further the robot system 100 according to the first embodiment is configured so that during the automatic operation of the slave arm 1, the operation of the slave arm 1 is correctable by an operator manipulating the manipulator 22.

Here, in this specification, the control mode in which the slave arm 1 operates according to a preset task program is referred to as "automatic operation mode." In the automatic operation mode, similar to a conventional teaching playback robot, the slave arm 1 automatically performs a given work without the operator manipulating the operating device 2.

Moreover, in this specification, the control mode in which the slave arm 1 operates based on the operation of the operator received by the manipulator 22 of the operating device 2 is referred to as "manual operation mode." Note that, in the manual operation mode, the slave arm 1 may be operated to completely follow a manipulating instruction received from the manipulator 22, or the slave arm 1 may be operated while correcting the manipulating instruction received from the manipulator 22 with a preset program (e.g., hand shake correction).

Furthermore, in this specification, the control mode in which the slave arm 1 operating according to the preset task program is corrected by the operator's manipulation of received by the manipulator 22 is referred to as "automatic operation correcting mode."

Hereinafter, respective devices constituting the robot system 100 according to the first embodiment are described in detail.

The slave arm 1 is a robot which is installed in a workspace and performs a series of works comprised of a plurality of processes. Note that the series of works comprised of the plurality of processes may include works, such as assembling of component(s) to a product and painting.

The slave arm 1 according to the first embodiment is an articulated robot, in a line production or a cell production, which is utilized at a production plant where products are produced by assembling electric and/or electronic components etc., is disposed along a workbench provided to the production plant, and is capable of performing at least one of works, such as transferring, assembling or relocating of component(s), and converting the posture, to workpiece(s) on the workbench. Note that the embodiment of the slave arm 1 is not limited to the configuration described above, but may be widely applied to any articulated robots, regardless of a horizontal articulated type or a vertical articulated type.

Here, a specific configuration of the slave arm 1 will be described with reference to FIG. 2.

Figure 2:
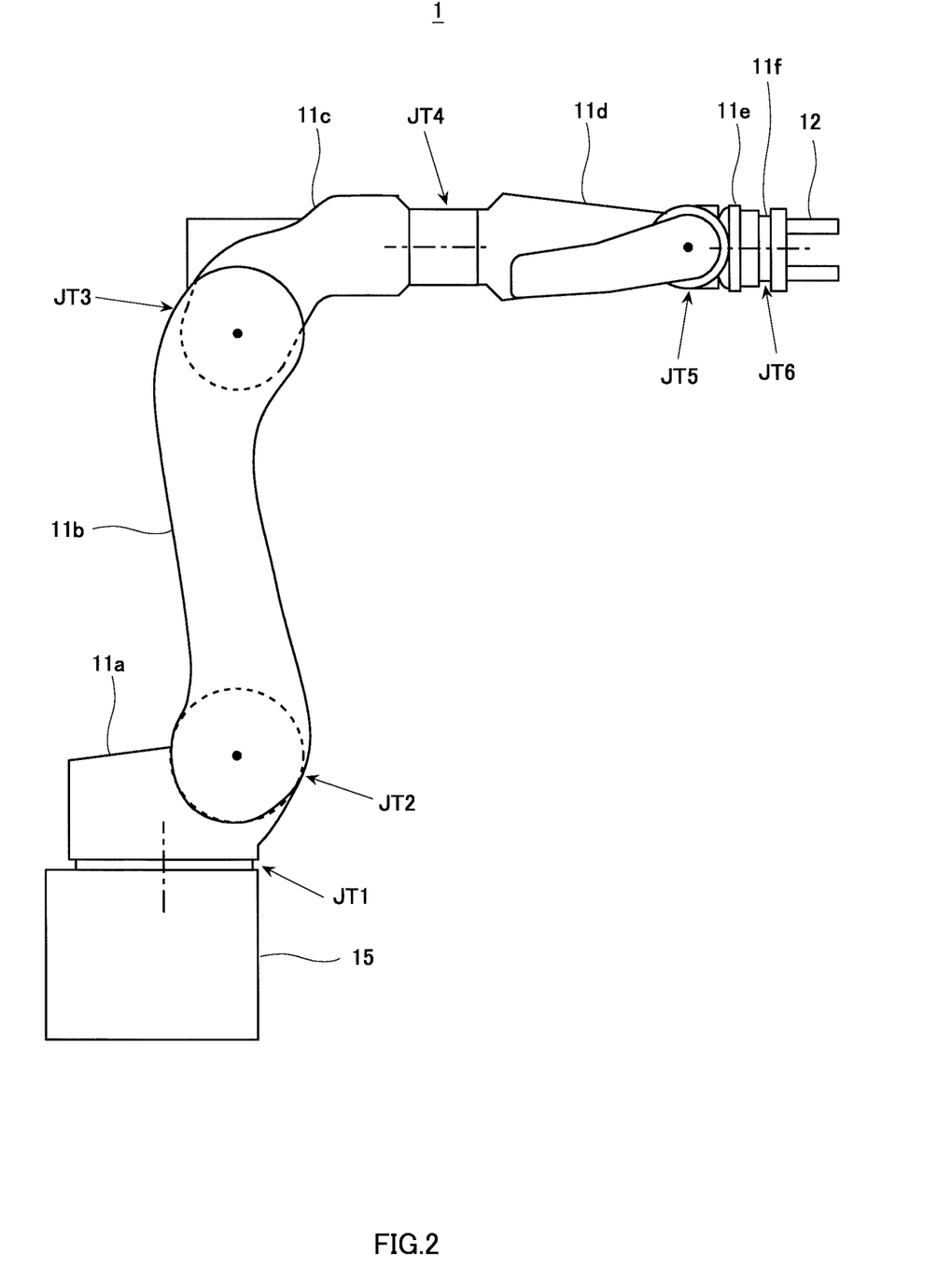
FIG. 2 is a schematic diagram illustrating a schematic configuration of a slave arm illustrated in FIG. 1.

FIG. 2 is a schematic diagram illustrating a schematic configuration of the slave arm illustrated in FIG. 1.

As illustrated in FIG. 1, the slave arm 1 is an articulated robot arm having a coupled body of a plurality of links (here, a first link 11a to a sixth link 11f), a plurality of joints (here, a first joint JT1 to a sixth joint JT6), and a pedestal 15 supporting them.

At the first joint JT1, the pedestal 15 and a base-end part of the first link 11a are coupled to each other so as to be rotatable about an axis extending vertically. At the second joint JT2, a tip-end part of the first link 11a and a base-end part of the second link 11b are coupled to each other so as to be rotatable about an axis extending horizontally. At the third joint JT3, a tip-end part of the second link 11b and a base-end part of the third link 11c are coupled to each other so as to be rotatable about an axis extending horizontally.

Further, at the fourth joint JT4, a tip-end part of the third link 11c and a base-end part of the fourth link 11d are coupled to each other so as to be rotatable about an axis extending in the longitudinal directions of the fourth link 11d. At the fifth joint JT5, a tip-end part of the fourth link 11d and a base-end part of the fifth link 11e are coupled to each other so as to be rotatable about an axis perpendicular to the longitudinal directions of the fourth link 11d. At the sixth joint JT6, a tip-end part of the fifth link 11e and a base-end part of the sixth link 11f are twistably and rotatably coupled to each other.

A mechanical interface is provided at a tip-end part of the sixth link 11f Detachably attached to this mechanical interface is an end effector 12 corresponding to the contents of work.

Further, the first joint JT1 to the sixth joint JT6 are provided with drive motors M1-M6 as an example of actuators for relatively rotating two members to which each joint is connected, respectively. The drive motors M1-M6 may be, for example, servo motors which are servo-controlled by the control device 4. Moreover, the first joint JT1 to the sixth joint JT6 are provided with rotation sensors E1-E6 which detect rotational positions of the drive motors M1-M6 (see FIG. 4), and current sensors C1-C6 which detect currents for controlling the rotations of the drive motors M1-M6 (see FIG. 4), respectively. The rotation sensors E1-E6 may be, for example, encoders. Note that the description of the drive motors M1-M6, the rotation sensors E1-E6, and the current sensors C1-C6 described above are denoted by attaching the suffix of 1-6 to the alphabet corresponding to each of the joints JT1-JT6. Hereinafter, when an arbitrary joint is illustrated among the joints JT1-JT6, the joint is referred to as "joint JT" while omitting the suffix, and the same is applied to the drive motor M, the rotation sensor E, and the current sensor C.

As described above, the operating device 2 has the teaching pendant 21 and the manipulator 22. Since the teaching pendant 21 has the same structure as a known teaching pendant, detailed description thereof is omitted. Note that in the first embodiment, the teaching pendant 21 and the manipulator 22 are disposed in two different casings, respectively.

The manipulator 22 is a device for receiving the manipulating instruction from the operator. Further, when operating the slave arm 1 in the manual operation mode or the automatic operation correcting mode, the manipulator 22 outputs to the control device 4 operation instruction values, such as positional information, attitude information, moving direction, moving speed of the slave arm 1, etc. by the operator's manipulation. The manipulator 22 may be, for example, a master arm, a joystick, or a tablet computer. Note that the manipulator 22 may be separately provided with an input part which inputs a start instruction of work, a notice of completion of the work by a manual operation, etc., an adjuster 22a which adjusts a second coefficient B (see FIG. 4) etc. The adjuster 22a may include, for example, a volume knob.

The storage device 5 is a readable and writable recording medium, which stores a task program 51 and operation sequence information 52 of the robot system 100. Note that, although in the robot system 100 according to the first embodiment, the storage device 5 is provided separately from the control device 4, it may be integrally provided with the control device 4.

The task program 51 is created by, for example, teaching by the operator using the teaching pendant 21, and stored in the storage device 5 in association with identification information on the slave arm 1 and the task. Note that the task program 51 may be created as an operation flow for each work.

The operation sequence information 52 is information regarding an operation sequence which defines a series of work processes performed by the slave arm 1 in the workspace. In the operation sequence information 52, an operation order of the work process and the control mode of the slave arm 1 are associated with each other. Further, in the operation sequence information 52, the task program for causing the slave arm 1 to automatically perform the work is associated with each work process. Note that the operation sequence information 52 may include a program for causing the slave arm 1 to automatically perform the work for each work process.

The control device 4 controls the operation of the slave arm 1, and includes a transceiver 40, a motion controller 41, and an automatic operation correcting means 42 having an adder 42a as functional blocks. The control device 4 may be comprised of, for example, an arithmetic part (not illustrated), such as a microcontroller, an MPU and a PLC (Programmable Logic Controller), a logic circuit, etc., and a memory part (not illustrated), such as a ROM or a RAM. Moreover, each functional block provided to the control device 4 is implementable by the arithmetic part of the control device 4 reading and executing the program stored in a memory part or the storage device 5.

Note that the control device 4 may not only be in a form comprised of a single control device, but also in a form comprised of a group of control devices in which a plurality of control devices collaborate with each other to execute the control of the slave arm 1 (robot system 100).

The transceiver 40 receives an input signal transmitted from the outside of the control device 4 and, for example, transmits an output signal from the control device 4 to the slave arm 1 etc. The input signal received by the transceiver 40 may be, for example, a signal transmitted from the operating device 2, a signal transmitted from a manipulating instruction part (not illustrated) other than the operating device 2, or a position signal of the slave arm 1 transmitted from the rotation sensor E of the slave arm 1 described later (positional information), etc. Moreover, the output signal transmitted from the transceiver 40 may include, for example, an operational instructing signal for instructing the operation of the slave arm 1 (operation instruction value; positional information, speed information, torque value, etc.).

When the transceiver 40 receives the manipulating instruction from the manipulator 22 as the input signal, the motion controller 41 determines the operating mode of the process which the slave arm 1 carries out in the series of works by using the manipulating instruction as a trigger. The motion controller 41 is capable of performing the determination of the operating mode of the process which the slave arm 1 carries out next, with reference to the operation sequence information 52 stored in the storage device 5. Once the motion controller 41 determines the operating mode, it controls the slave arm 1 so that the slave arm 1 operates in the determined operating mode.

For example, if the motion controller 41 determines that the slave arm 1 is to be operated in the automatic operation mode, it controls the slave arm 1 to perform operation defined by the task program 51 or, by reading the operation sequence information 52, operation defined by a program contained in the operation sequence information 52.

Further, if the motion controller 41 determines that the slave arm 1 is to be operated in the manual operation mode, it controls the slave arm 1 to perform the operation based on the manipulating instruction received from the manipulator 22 by the transceiver 40.

Further, if the motion controller 41 determines that the slave arm 1 is to be operated in the automatic operation correcting mode, it performs the operation defined by the task program 51 or, by reading the operation sequence information 52, the operation defined by the program contained in the operation sequence information 52, and when the transceiver 40 receives a correction instructing signal as the input signal from the manipulator 22 during the operation of the slave arm 1 by the automatic operation mode, the operation of the slave arm 1 by the automatic operation is corrected to operation following the correction instructing signal from the manipulator 22.

Then, when the output of the correction instructing signal from the manipulator 22 is stopped and the transceiver 40 stops receiving the correction instructing signal, or when the transceiver 40 receives an instruction for resuming the automatic operation of the slave arm 1 from the manipulator 22, the motion controller 41 resumes the automatic operation of the slave arm 1.

When the transceiver 40 receives the correction instructing signal (operation instruction value; correction instruction value) during the automatic operation of the slave arm 1, the automatic operation correcting means 42 instructs the motion controller 41 to correct the operation of the slave arm 1. Note that a specific method of correcting the operation of the slave arm 1 will be described later.

[Operation and Effect of Robot System]

Next, operation and effect of the robot system 100 according to the first embodiment are described with reference to FIGS. 1 to 4. Note that since the operation of performing the series of works by the operator manipulating the manipulator 22 to operate the slave arm 1 is executed similar to a known robot system, detailed description thereof is omitted. Moreover, the following operation is executed by the arithmetic part of the control device 4 reading the program stored in the memory part of the control device 4 or the storage device 5.

Figure 3:
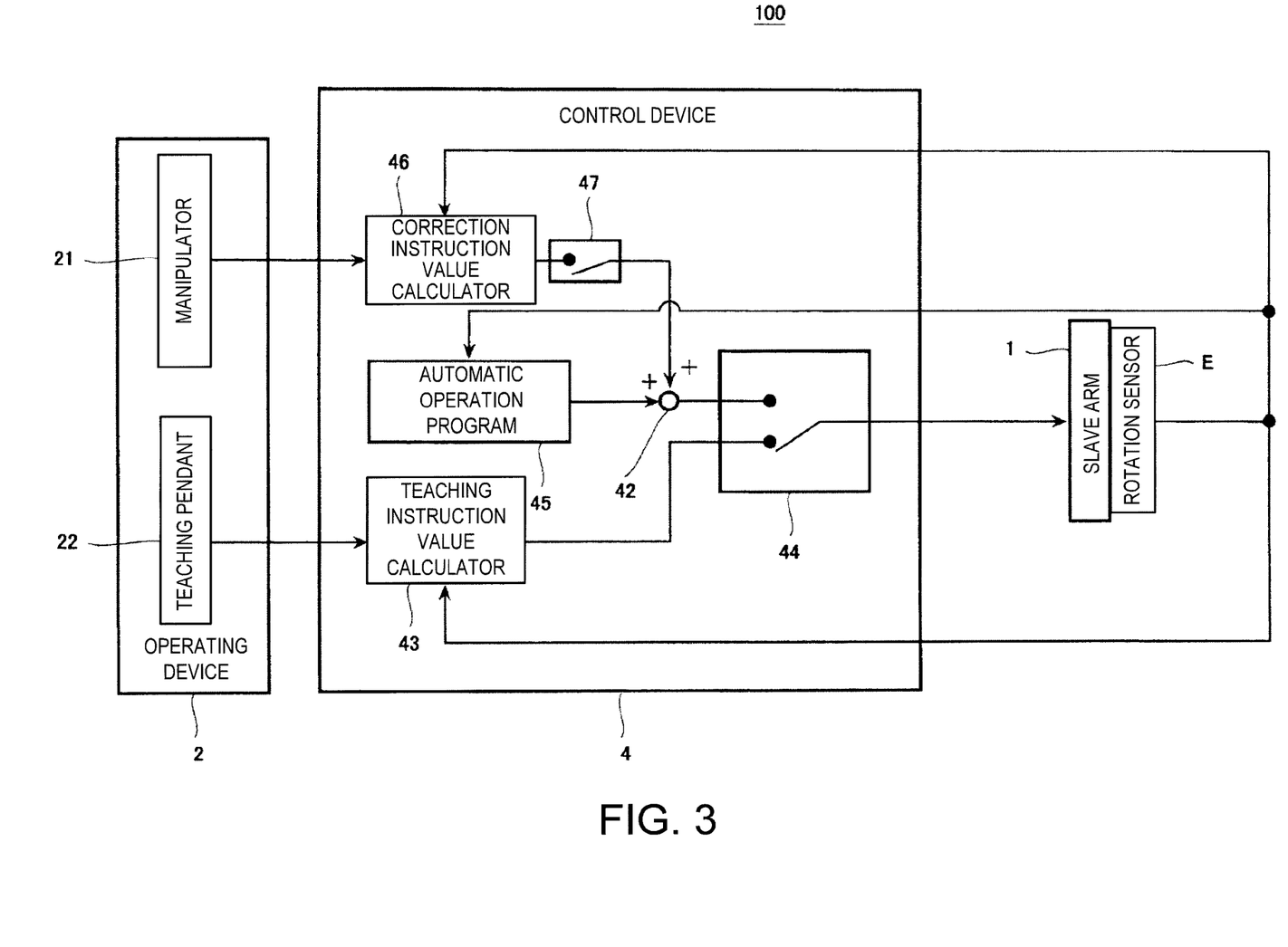
FIG. 3 is a block diagram illustrating one example of a control system of the robot system according to the first embodiment.

FIG. 3 is a block diagram illustrating one example of a control system of the robot system according to the first embodiment.

First, a flow of signal when the operator manipulates the teaching pendant 21 to perform teaching is described with reference to FIG. 3.

When the operator manipulates the teaching pendant 21 to input numeric values such as the position coordinates of the slave arm 1 or the angles of the first joint JT1 to the sixth joint JT6, etc., the position coordinate information on the slave arm 1 or the angular information on the first joint JT1 to the sixth joint JT6 (the attitude information on the slave arm 1) are inputted to a teaching instruction value calculator 43. The teaching instruction value calculator 43 calculates an output amount of current (current value) for operating the drive motor M disposed at each joint based on the position coordinate information or the angular information, and outputs the current value to a switch device 44.

The switch device 44 is configured to switch the current value between the current value inputted from the teaching instruction value calculator 43 and the current value inputted from an automatic operation program 45 described later or the automatic operation correcting means 42 and output it to the slave arm 1. Note that the switch device 44 may adopt a form in which the inputted current value is switched by a given program and outputted to the slave arm 1, or a form in which the input destination is electrically switched (changed) by a switch (element). Moreover, a form in which the switch device 44 is configured by having a protocol of the current value outputted from the teaching instruction value calculator 43 different from a protocol of the current value outputted from the automatic operation program 45 or the automatic operation correcting means 42, may be adopted.

The switch device 44 outputs the current value inputted from the teaching instruction value calculator 43 to the slave arm 1. Thus, in the slave arm 1, the drive motor M disposed at each joint rotates so that the angles of the first joint JT1 to the sixth joint JT6 become target angles. Here, the rotation sensor E disposed at each joint detects the angle of the joint and feeds back the detected angle to the teaching instruction value calculator 43. Then, the teaching instruction value calculator 43 calculates the position coordinates of the slave arm 1 based on the angle of each joint inputted from the rotation sensor E. The calculated position coordinates of the slave arm 1 are stored in the task program 51 of the storage device 5.

In this manner, the operator manipulates the teaching pendant 21 to define the operation of the slave arm 1, sets the position coordinates of the slave arm 1 required for operating in the automatic operation mode, and creates the task program 51.

Next, the flow of signal when the operator manipulates the manipulator 22 to correct the operation of the slave arm 1 during the automatic operation of the slave arm 1, that is, when executing the automatic operation correcting mode, is described with reference to FIGS. 3 and 4.

First, a case is considered where the control device 4 reads the task program 51 created as described above to execute the automatic operation program 45. Here, based on the position coordinate information on the slave arm 1 or the angle information on the first joint JT1 to the sixth joint JT6 stored in the task program 51, the automatic operation program 45 calculates the current value for operating the motor M disposed at each joint, and outputs the current value to the switch device 44.

The switch device 44 outputs the current value inputted from the automatic operation program 45 to the slave arm 1. Thus, in the slave arm 1, the drive motor M disposed at each joint rotates so that the angles of the first joint JT1 to the sixth joint JT6 become the target angles. Here, the rotation sensor E disposed at each joint detects the angle of the joint and feeds back the detected angle to the automatic operation program 45. Then, the automatic operation program 45 calculates the position coordinates of the slave arm 1 based on the angle of each joint inputted from the rotation sensor E.

In the considered case, while the automatic operation of the slave arm 1 is executed, the operator manipulates the manipulator 22 to output the correction instructing signal (correction instruction value) for correcting the operation of the slave arm 1 to a correction instruction value calculator 46. Note that the manipulator 22 is capable of outputting the positional information, the attitude information, the moving direction, the moving speed of the slave arm 1, etc., and here, a case where the positional information (position coordinate information) is outputted to the correction instruction value calculator 46 is described.

In this case, the correction instruction value calculator 46 outputs the position coordinate information inputted from the manipulator 22 to the automatic operation correcting means 42 via a switch device 47. Note that the switch device 47 may adopt a form in which whether to output the inputted position coordinate information to the automatic operation correcting means 42 is switched by a given program, or a form in which whether to output the electrically inputted position coordinate information to the automatic operation correcting means 42 is switched by a switch.

Based on the position coordinate information inputted from the automatic operation program 45 (hereinafter, referred to as the position instruction value $\Delta P1$) and the position coordinate information inputted from the correction instruction value calculator 46 (hereinafter, referred to as the correction instruction value $\Delta P2$), the automatic operation correcting means 42 calculates the current value for operating the drive motor M disposed at each joint and outputs the current value to the switch device 44.

Here, the automatic operation correcting means 42 will be described in more detail with reference to FIG. 4.

Figure 4:
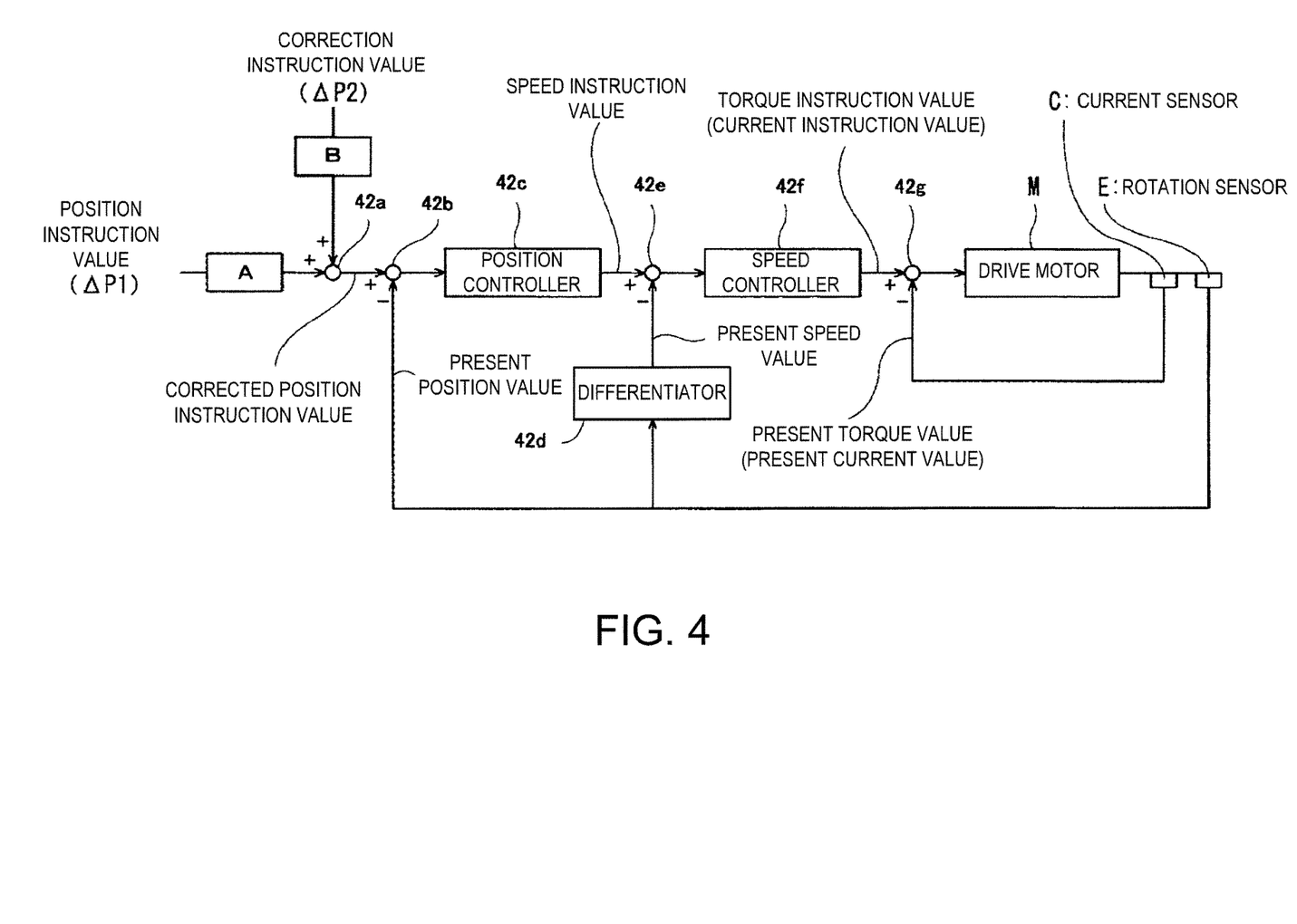
FIG. 4 is a block diagram illustrating one example of a control system of an automatic operation correcting means illustrated in FIGS. 1 and 3.

FIG. 4 is a block diagram illustrating one example of a control system of the automatic operation correcting means illustrated in FIGS. 1 and 3.

As illustrated in FIG. 4, the automatic operation correcting means 42 includes the adder 42a, subtractors 42b, 42e and 42g, a position controller 42c, a differentiator 42d, and a speed controller 42f.

The adder 42a adds $\Delta P2$ to $\Delta P1$ to generate a corrected position instruction value. Here, the adder 42a generates the position instruction value according to the following Equation (1).

$$\Delta P0 = A \times \Delta P1 + B \times \Delta P2 \qquad \text{Equation (1)}$$

Here, a first coefficient A and the second coefficient B are variables, and they are in a relationship in which when one of the coefficients increases, the other coefficient decreases. More specifically, the first coefficient A and the second coefficient B may be coefficients with which a value obtained by multiplying the first coefficient A and the second coefficient B becomes a first given preset value, or coefficients with which a value obtained by adding the first coefficient A and the second coefficient B becomes a second given preset value. Note that the first given value or the second given value may be 1, 10 or 100.

The subtractor 42b subtracts a present position value detected by the rotation sensor E from the corrected position instruction value to generate an angle deviation. The subtractor 42b outputs the generated angle deviation to the position controller 42c.

The position controller 42c generates a speed instruction value from the angle deviation inputted from the subtractor 42b by arithmetic processing based on a predetermined transfer function or proportional coefficient. The position controller 42c outputs the generated speed instruction value to the subtractor 42e.

The differentiator 42d differentiates the present position value information detected by the rotation sensor E to generate a change amount of the rotation angle of the drive motor M per unit time, that is, the present speed value. The differentiator 42d outputs the generated present speed value to the subtractor 42e.

The subtractor 42e subtracts the present speed value inputted from the differentiator 42d from the speed instruction value inputted from the position controller 42c to generate a speed deviation. The subtractor 42e outputs the generated speed deviation to the speed controller 42f.

The speed controller 42f generates a torque instruction value (current instruction value) from the speed deviation inputted from the subtractor 42e by arithmetic processing based on a predetermined transfer function or proportional coefficient. The speed controller 42f outputs the generated torque instruction value to the subtractor 42g.

The subtractor 42g subtracts a present current value detected by the current sensor C from the torque instruction value inputted from the speed controller 42f to generate a current deviation. The subtractor 42g outputs the generated current deviation to the drive motor M to drive the drive motor M.

Note that, as described above, the second coefficient B may be inputted to the automatic operation correcting means 42 by the operator manually adjusting the adjuster 22a provided to the manipulator 22 of the operating device 2. Further, as the adjuster 22a, for example, a program for causing the second coefficient B to be 0 at a great distance from the work target (a structure to which a workpiece is attached, etc.), and gradually increase as approaching the work target may be stored in advance in the storage device 5.

Moreover, the second coefficient B may be a variable which becomes, after a value is inputted from the adjuster 22a to the automatic operation correcting means 42, the inputted value over a given period of time, or a variable which becomes, after the correction instruction value ΔP2 is inputted from the manipulator 22 to the automatic operation correcting means 42, a preset value over a given period of time. For example, in view of preventing the correction of the operation of the slave arm 1 from being sharp, the given time period may be 0.5 seconds or more, or may be 1 second or more. Further, in view of the operator acknowledging that the corrected operation of the slave arm 1 is reflected, the given time period may be within 2 seconds, within 3 seconds, or within 5 seconds.

Specifically, for example, the second coefficient B may be such a variable that a relationship between a lapsed period of time since the value is inputted from the adjuster 22a to the automatic operation correcting means 42 or the correction instruction value ΔP2 is inputted from the manipulator 22 to the automatic operation correcting means 42 and a change amount ΔB per unit time corresponds to a linear function. Further, the second coefficient B may be such a variable that the relationship between the lapsed time period and the change amount ΔB per unit time corresponds to a high-dimensional function, such as a quadratic function or a cubic function, or it corresponds to a logarithmic function. Furthermore, the second coefficient B may be such a variable that the relationship between the lapsed time period and the change amount ΔB per unit time increases stepwise.

Thus, it is possible to prevent that when the correction instruction value ΔP2 is inputted from the manipulator 22 to the automatic operation correcting means 42, the operation of the slave arm 1 is sharply corrected and the slave arm 1 operates in an unexpected direction.

In this manner, the automatic operation correcting means 42 calculates the current value for operating the drive motor M disposed at each joint (current deviation), and outputs the current value to the switch device 44 (see FIG. 3). The switch device 44 outputs the current value inputted from the automatic operation correcting means 42 to the slave arm 1.

Thus, in the slave arm 1, the drive motor M disposed at each joint rotates so that the angles of the first joint JT1 to the sixth joint JT6 become the target angles. Here, the rotation sensor E disposed at each joint detects the angle of the joint and feeds back the detected angle to the correction instruction value calculator 46. Then, the correction instruction value calculator 46 calculates the position coordinates of the slave arm 1 based on the angle of each joint inputted from the rotation sensor E.

With the robot system 100 according to the first embodiment configured as described above, in the conventional industrial robot including the teaching pendant, the manipulator 22 is used to correct the preset operation of the robot. Since the manipulator 22 is capable of outputting the position information, the attitude information, the moving direction, the moving speed, etc. of the slave arm 1, it is possible to reduce the workload on the operator compared with a case of correcting the operation of the robot by using the teaching pendant 21.

Note that in the first embodiment, a form in which the position coordinate information is inputted as the correction instruction value ΔP2 from the correction instruction value calculator 46 to the automatic operation correcting means 42 is adopted, but it is not limited to this. For example, a form in which ΔP2 is the speed instruction value may be adopted, or a form in which ΔP2 is the torque instruction value may be adopted.

When ΔP2 is the speed instruction value, a value obtained by multiplying the speed instruction value as ΔP2 by the second coefficient B (manual speed instruction value) is inputted to the subtractor 42e. Further, the subtractor 42e is supplied with a value which the position controller 42c obtains by multiplying the speed instruction value generated based on the operational instruction for the robot in the automatic operation (ΔP1; position instruction value) and a present position value, by the first coefficient A (corrected speed instruction value). Furthermore, the subtractor 42e is supplied with a present speed value generated by the differentiator 42d, from this differentiator 42d.

Then, the subtractor 42e adds the corrected speed instruction value to the inputted manual speed instruction value and generates the speed deviation based on the value obtained by subtracting the present speed value. Note that the operation after the subtractor 42e generates the speed deviation is executed in the similar manner to that described above.

Similarly, when ΔP2 is the torque instruction value, a value obtained by multiplying the torque instruction value as ΔP2 by the second coefficient B (manual torque instruction value) is inputted to the subtractor 42g. Further, the subtractor 42g is supplied with a value obtained by multiplying the torque instruction value generated by the speed controller 42f by the first coefficient A based on the speed deviation inputted to the speed controller 42f via the position controller 42c and the subtractor 42e in response to the operational instruction for the robot in the automatic operation (ΔP1; position instruction value) (corrected torque instruction value). Furthermore, the subtractor 42g is supplied with the present current value detected by the current sensor C.

Then, the subtractor 42g adds the corrected torque instruction value to the inputted manual torque instruction value and subtracts the present current value to generate the current deviation. The subtractor 42g sends the generated current deviation to the drive motor M to drive the drive motor M.

Second Embodiment

A robot system according to a second embodiment is configured so that, in the robot system according to the first embodiment, the control device has a common connection terminal connected to the teaching device or the manipulator, and when teaching the control device the positional information on the robot main body or the angular information on the plurality of joints, the teaching device is connected to the common connection terminal to manually operate the robot main body, or when correcting the operation of the robot main body under the automatic operation, the manipulator is connected to the common connection terminal.

Hereinafter, one example of the robot system according to the second embodiment is described with reference to FIG. 5.
[Configuration of Robot System]

Figure 5:
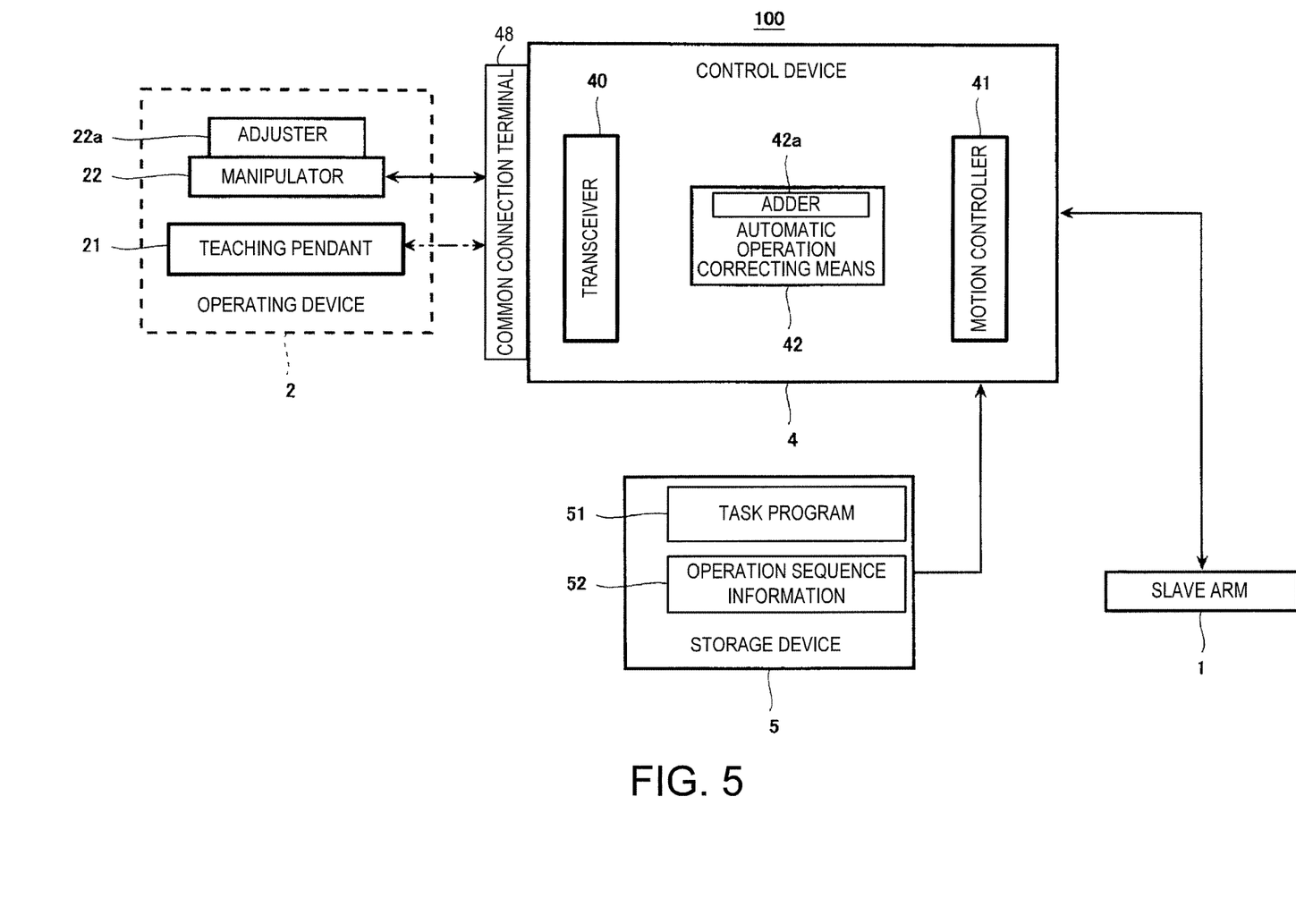
FIG. 5 is a block diagram illustrating a schematic configuration of a robot system according to a second embodiment.

FIG. 5 is a block diagram illustrating a schematic configuration of the robot system according to the second embodiment.

As illustrated in FIG. 5, the robot system 100 according to the second embodiment has the same basic configuration as the robot system 100 according to the first embodiment, but it is different in that the control device 4 has a common connection terminal 48 for connecting with the teaching pendant 21 or the manipulator 22. When teaching the control device 4 the positional information on the slave arm 1 or the angular information on the plurality of joints, the operator connects the teaching pendant 21 to the common connection terminal 48 to manually operate the slave arm 1, or when correcting the operation of the slave arm 1 under the automatic operation, the operator connects the manipulator 22 to the common connection terminal 48.

Even with the robot system 100 according to the second embodiment configured as above, similar operations and effects to those of the robot system 100 according to the first embodiment are obtained.

Note that the common connection terminal 48 may be configured so that while one device between the teaching pendant 21 and the manipulator 22 is connected thereto, the other device cannot be connected, or both of the teaching pendant 21 and the manipulator 22 are connectable at the same time.
[First Modification]

Next, one modification of the robot system 100 according to the second embodiment will be described with reference to FIG. 6.

The robot system according to a first modification of the second embodiment further includes a first switch device 6 which switches the instruction value between the teaching instruction value outputted from the teaching device and the operation instruction value outputted from the manipulator, and outputs it to the control device.

Figure 6:
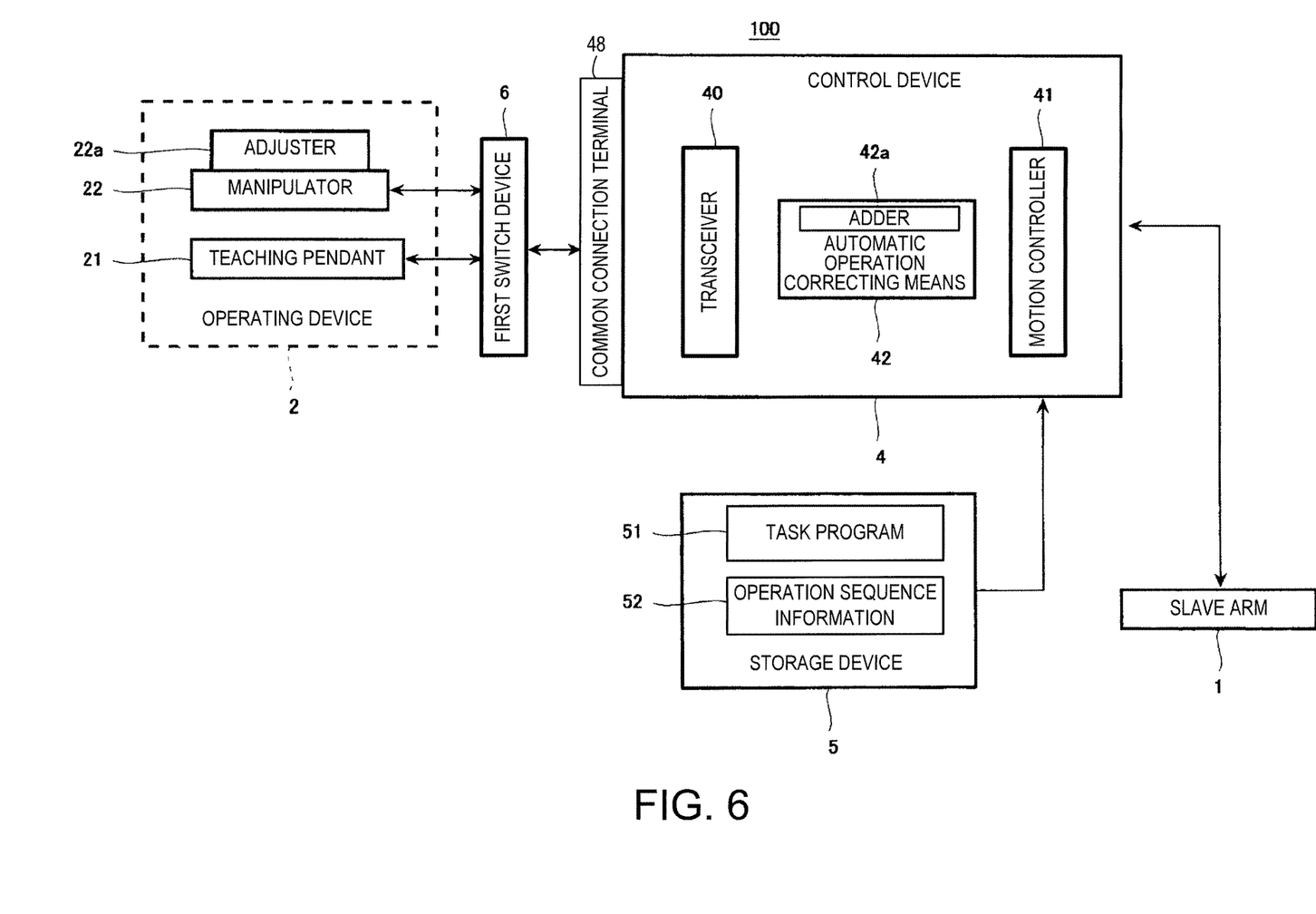
FIG. 6 is a block diagram illustrating a schematic configuration of a robot system according to a first modification of the second embodiment.

FIG. 6 is a block diagram illustrating a schematic configuration of the robot system according to the first modification of the second embodiment.

As illustrated in FIG. 6, the robot system 100 according to the first modification has the same basic configuration as the robot system according to the second embodiment, but is different in that it further includes a first switch device 6 which switches the instruction value between the teaching instruction value outputted from the teaching pendant 21 and the operation instruction value outputted from the manipulator 22, and outputs it to the control device 4. An output terminal of the teaching pendant 21 and an output terminal of the manipulator 22 are respectively electrically-connected to an input terminal of the first switch device 6. Further an output terminal of the first switch device 6 is electrically connected to the common connection terminal 48 of the control device 4.

Additionally, the first switch device 6 may adopt a form in which the inputted instruction value is switched by a given program and outputted to the common connection terminal 48 of the control device 4, or a form in which the input destination is electrically switched (changed) by a switch (element).

Even with the robot system 100 according to the first modification configured as above, similar operations and effects to those of the robot system 100 according to the second embodiment are obtained.

Third Embodiment

A robot system according to a third embodiment is configured so that, in the robot system according to the first embodiment, the correction instruction value outputted from the manipulator is inputted to the control device via the teaching device.

Hereinafter, one example of the robot system according to the third embodiment is described with reference to FIG. 7.
[Configuration of Robot System]

Figure 7:
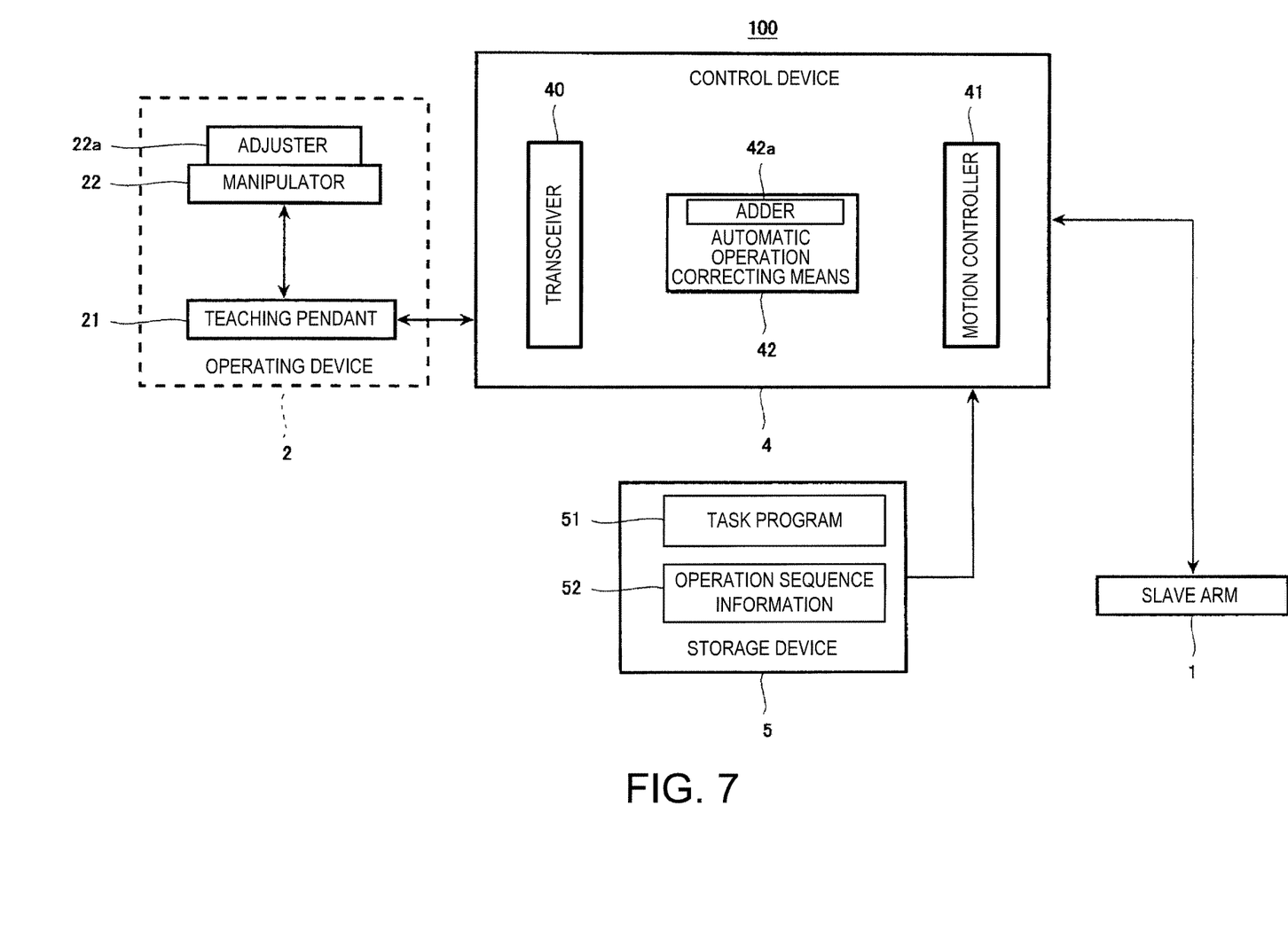
FIG. 7 is a block diagram illustrating a schematic configuration of a robot system according to a third embodiment.

FIG. 7 is a block diagram illustrating a schematic configuration of the robot system according to the third embodiment.

As illustrated in FIG. 7, the robot system 100 according to the third embodiment has the same basic configuration as the robot system 100 according to the first embodiment, but it is different in that the correction instruction value outputted from the manipulator 22 and the adjuster 22a is inputted to the control device 4 via the teaching pendant 21.

Even with the robot system 100 according to the third embodiment configured as above, similar operations and effects to those of the robot system 100 according to the first embodiment are obtained.

Fourth Embodiment

A robot system according to a fourth embodiment is configured so that, in the robot system according to any one of the first to third embodiments, the teaching device and the manipulator are disposed in a single casing.

Further, in the robot system according to the fourth embodiment, the operating device may further have an instruction value generator which generates a teaching instruction value to be outputted from the teaching device and the operation instruction value to be outputted from the manipulator.

Hereinafter, one example of the robot system according to the fourth embodiment is described with reference to FIG. 8.
[Configuration of Robot System]

Figure 8:
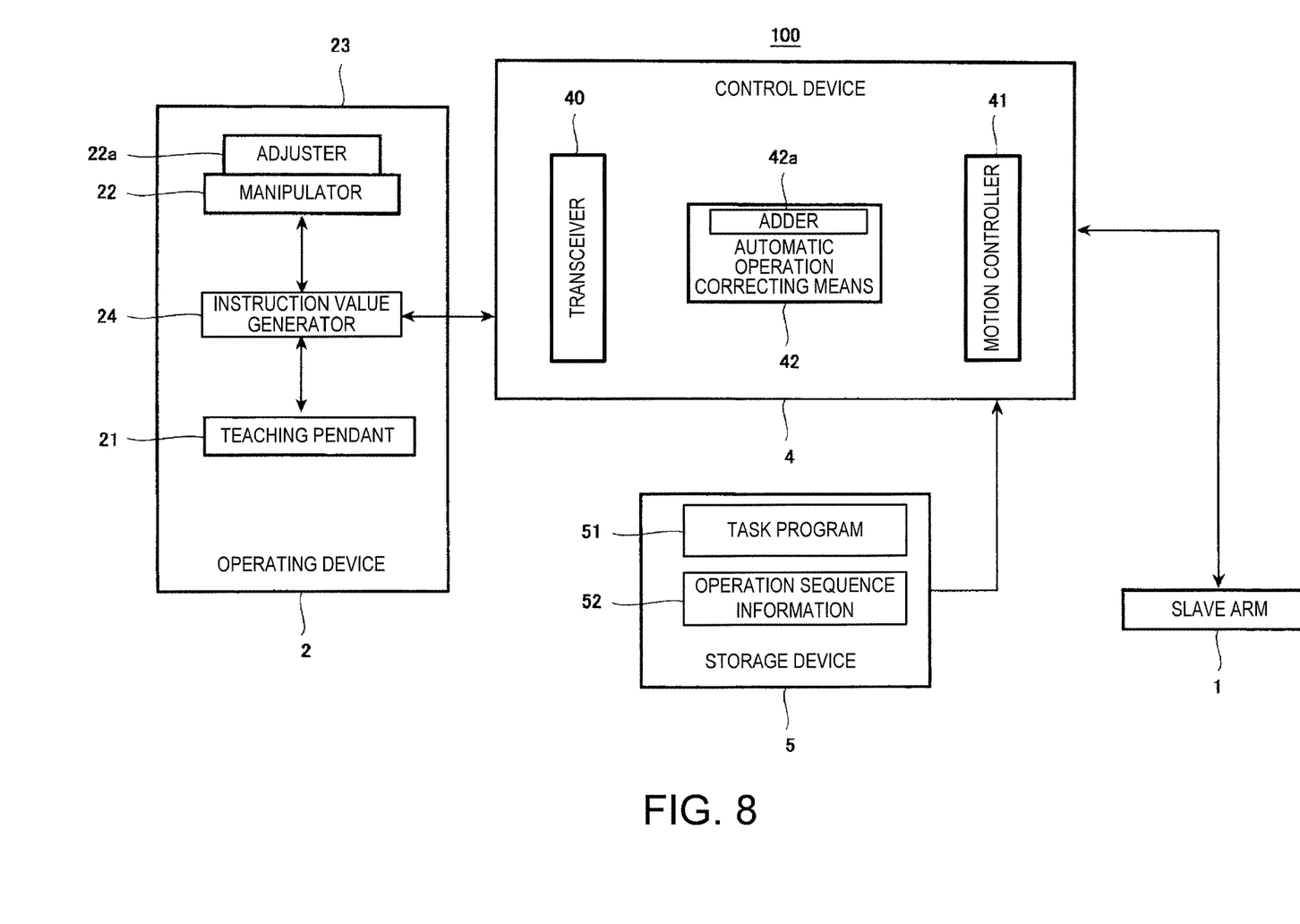
FIG. 8 is a block diagram illustrating a schematic configuration of a robot system according to a fourth embodiment.

FIG. 8 is a block diagram illustrating a schematic configuration of the robot system according to the fourth embodiment.

As illustrated in FIG. 8, the robot system 100 according to the fourth embodiment has the same basic configuration as the robot system 100 according to the first embodiment, but it is different in that the teaching pendant 21, the manipulator 22 and the adjuster 22a are disposed in a single casing 23, and that the operating device 2 further has an instruction value generator 24.

The instruction value generator 24 has a function for generating instruction values, such as the position coordinate information or the angular information to be outputted to the control device 4, based on numeric values, such as the position coordinates of the slave arm 1 or the angles of the first joint JT1 to the sixth joint JT6, etc. inputted by the operator manipulating the teaching pendant 21. Moreover, the instruction value generator 24 has a function for generating instruction values, such as the position coordinate information etc. to be outputted to the control device 4, based on the positional information, the attitude information, the moving direction, the moving speed of the slave arm 1, etc. inputted by the operator manipulating the teaching pendant 21.

That is, the instruction value generator 24 generates the instruction values for both the information inputted to the teaching pendant 21 and the information inputted to the manipulator 22, switches the respective instruction values therebetween, and outputs it to the control device 4. Here, the instruction value generator 24 generates the instruction values with different protocols so that the information from the teaching pendant 21 and the information from the manipulator 22 are differentiable from each other.

Even with the robot system 100 according to the fourth embodiment configured as above, similar operations and effects to those of the robot system according to the first embodiment are obtained.

Fifth Embodiment

A robot system according to a fifth embodiment is configured so that in any one of the first to fourth embodiments, the teaching device has a function of the manipulator.

Further, in the robot system according to the fifth embodiment, the operating device may further have a second switch device which switches a function as the teaching device and a function as the manipulator therebetween.

Figure 9:
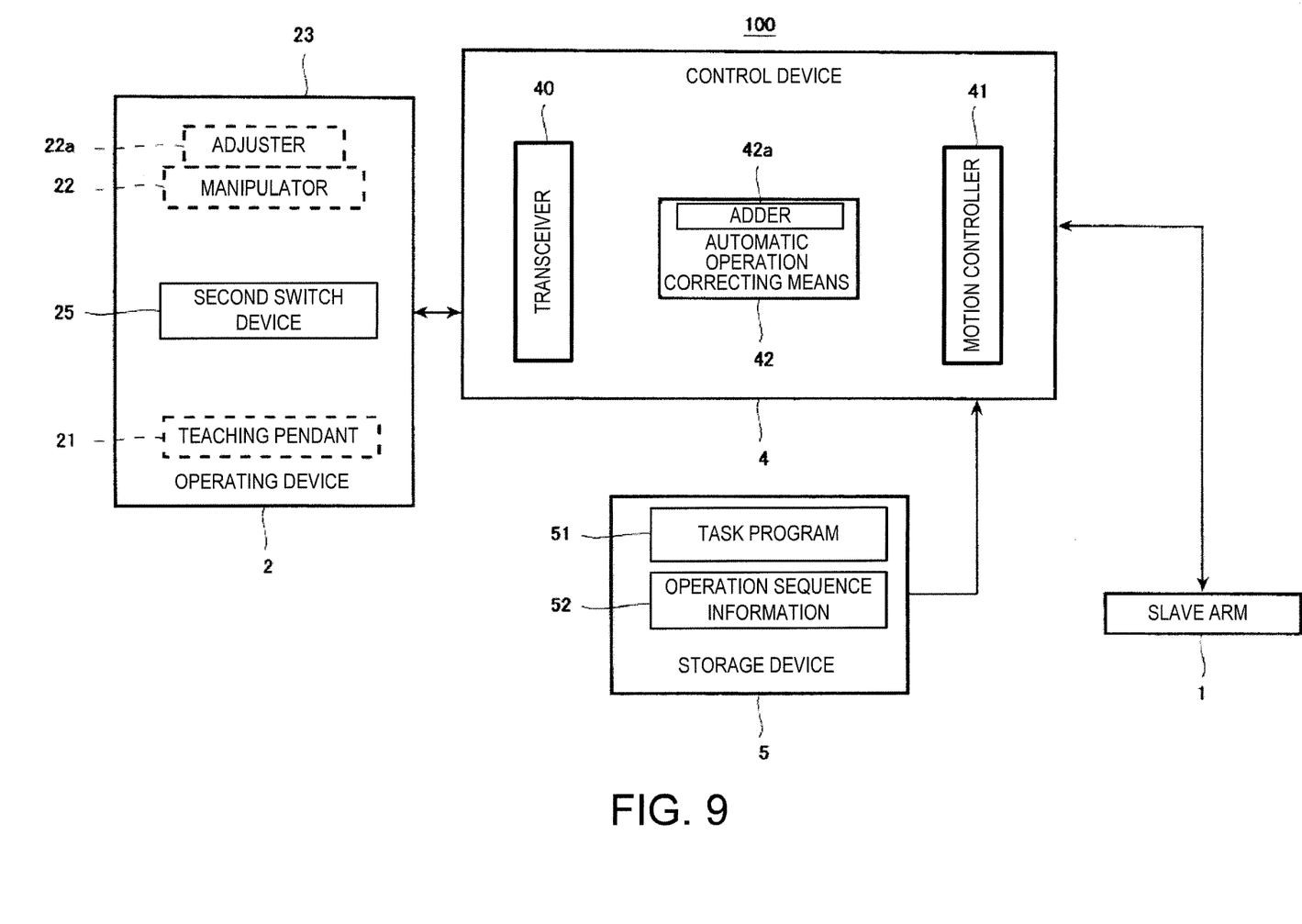
FIG. 9 is a block diagram illustrating a schematic configuration of a robot system according to a fifth embodiment.

Hereinafter, one example of the robot system according to the fifth embodiment is described with reference to FIG. 9.
[Configuration of Robot System]
FIG. 9 is a block diagram illustrating a schematic configuration of the robot system according to the fifth embodiment.

As illustrated in FIG. 9, the robot system 100 according to the fifth embodiment has the same basic configuration as the robot system 100 according to the first embodiment, but it is different in that the teaching pendant 21 has the function of the manipulator 22. In other words, the operating device 2 is configured to have both functions of the teaching pendant 21 and the manipulator 22.

For example, in order for the teaching pendant 21 to function as the manipulator 22, the operating device 2 (the teaching pendant 21) may be provided with buttons for inputting a numeric value of the position coordinates etc. of the slave arm 1 and, additionally, directional buttons, arrow keys, a lever, a stick, etc. for inputting the moving direction etc. of the slave arm 1.

Further, the robot system 100 according to the fifth embodiment is different from the robot system 100 according to the first embodiment in that a second switch device 25 is provided.

The second switch device 25 is a switch for the operator to switch whether to cause the operating device 2 to function as the teaching pendant 21 or whether to cause it to function as the manipulator 22. When the operator manipulates the second switch device 25 so that the operating device 2 functions as the teaching pendant 21, the operating device 2 generates the instruction value of the teaching pendant 21 and outputs it to the control device 4. Further, when the operator manipulates the second switch device 25 so that the operating device 2 functions as the manipulator 22, the operating device 2 generates the instruction value of the teaching pendant 21 and outputs it to the control device 4. Here, the operating device 2 may generate the instruction values with different protocols so that the instruction value of the teaching pendant 21 and the instruction value of the manipulator 22 are differentiable from each other.

Even with the robot system 100 according to the fifth embodiment configured as above, similar operations and effects to those of the robot system 100 according to the first embodiment are obtained.

It is apparent for a person skilled in the art that many improvements or other embodiments of the present disclosure are possible from the above description. Therefore, the above description is to be interpreted only as illustration, and it is provided in order to teach a person skilled in the art the best mode in which the present disclosure is implemented. Details of the structures and/or functions of the present disclosure may be substantially changed without departing from the spirit of the present disclosure.

INDUSTRIAL APPLICABILITY

Since the robot system of the present disclosure is capable of reducing the workload on the operator and easily correcting the preset operation of the robot, it is useful in the field of industrial robot.

DESCRIPTION OF REFERENCE CHARACTERS

1 Slave Arm
2 Operating Device
4 Control Device
5 Storage Device
6 First Switch Device
11a First Link
11b Second Link
11c Third Link
11d Fourth Link
11e Fifth Link
11f Sixth Link
12 End Effector
15 Pedestal
21 Teaching Pendant
22 Manipulator
22a Adjuster
23 Casing
24 Instruction Value Generator
25 Second Switch Device
31b Subtractor
40 Transceiver
41 Motion Controller
42 Automatic Operation Correcting Means
42a Adder 42*b* Subtractor
42*c* Position Controller
42*d* Differentiator
42*e* Subtractor
42*f* Control Device
42*g* Subtractor
43 Teaching Instruction Value Calculator
44 Switch Device
45 Automatic Operation Program
46 Correction Instruction Value Calculator
47 Switch Device
48 Common Connection Terminal
51 Task Program
52 Operation Sequence Information
100 Robot System
JT1 First Joint
JT2 Second Joint
JT3 Third Joint
JT4 Fourth Joint
JT5 Fifth Joint
JT6 Sixth Joint
M Drive Motor

The invention claimed is:

1. A robot system comprising:
a robot main body having a plurality of joints;
a control device configured to control operation of the robot main body; and
an operating device including:
a teaching device configured to teach the control device one of positional information on the robot main body and angular information on the plurality of joints so as to execute an automatic operation of the robot main body; and
a manipulator configured to, during the automatic operation of the robot main body, receive a manipulating instruction inputted by an operator to manually operate the robot main body, the manipulating instruction manually inputted by the operator causing the control device to correct the operation of the robot main body by adjusting a movement of the robot main body during the automatic operation.

2. The robot system of claim 1, wherein:
the control device has a common connection terminal configured to connect to one of the teaching device and the manipulator,
when teaching the control device the one of the positional information on the robot main body and the angular information on the plurality of joints, the teaching device is connected to the common connection terminal, and
when manually operating the robot main body and correcting the operation of the robot main body under the automatic operation, the manipulator is connected to the common connection terminal.

3. The robot system of claim 1, further comprising a first switch device configured to switch between a teaching instruction value outputted from the teaching device and an operation instruction value outputted from the manipulator therebetween, the switch device being configured to output the respective teaching instruction value and the operation instruction value to the control device.

4. The robot system of claim 1, wherein an operation instruction value outputted from the manipulator is inputted to the control device via the teaching device.

5. The robot system of claim 1, wherein the operating device further includes an instruction value generator configured to generate a teaching instruction value to be outputted from the teaching device and an operation instruction value to be outputted from the manipulator.

* * * * *